US006968127B2

(12) United States Patent  (10) Patent No.: US 6,968,127 B2
Nanjyo  (45) Date of Patent: Nov. 22, 2005

(54) FUNDUS CAMERA

(75) Inventor: Tsuguo Nanjyo, Toyohashi (JP)

(73) Assignee: Nidek Co., Ltd., (JP)

( * ) Notice: Subject to any disclaimer, the term of this patent is extended or adjusted under 35 U.S.C. 154(b) by 0 days.

(21) Appl. No.: 09/940,582

(22) Filed: Aug. 29, 2001

(65) Prior Publication Data

US 2002/0025145 A1  Feb. 28, 2002

(30) Foreign Application Priority Data

Aug. 31, 2000 (JP) .............................. 2000-268428

(51) Int. Cl.⁷ .......................... A61B 3/14; G03B 29/00

(52) U.S. Cl. ....................................... 396/18; 351/208

(58) Field of Search ........................... 396/18, 14, 106, 396/323; 351/206, 207, 208, 221, 213, 214, 351/205, 209–212, 203; 348/78; 606/3, 4, 606/476; 600/476; 356/391, 394–397

(56) References Cited

U.S. PATENT DOCUMENTS

| 4,068,932 A | | 1/1978 | Ohta et al. .................. 351/206 |
| 5,037,194 A | | 8/1991 | Kohayakawa et al. ...... 351/224 |
| 5,543,865 A | * | 8/1996 | Nanjo ......................... 351/206 |
| 5,572,266 A | | 11/1996 | Ohtsuka ...................... 396/18 |
| 5,668,621 A | * | 9/1997 | Nanjo ......................... 351/206 |
| 6,082,859 A | | 7/2000 | Okashita et al. ............. 351/206 |
| 6,404,985 B1 | * | 6/2002 | Ohtsuka ...................... 396/18 |

FOREIGN PATENT DOCUMENTS

| EP | 1 138 256 A2 | 10/2001 |
| JP | SHO 63-022823 | 1/1988 |
| JP | HEI 9-173298 | 7/1997 |
| JP | HEI 9-276232 | 10/1997 |
| JP | HEI 11-169349 | 6/1999 |
| JP | HEI 11-313800 | 11/1999 |
| JP | 2000-189387 | 7/2000 |
| WO | WO 00/04820 | 2/2000 |

OTHER PUBLICATIONS

EPO Search Report dated Nov. 8, 2002.

* cited by examiner

Primary Examiner—Alan A. Mathews
Assistant Examiner—Rochelle Blackman
(74) Attorney, Agent, or Firm—Rader, Fishman & Grauer PLLC

(57) ABSTRACT

A fundus camera being capable of moving a fixation target surely and precisely to a position intended for photographing with an adequate degree of freedom for moving the fixation target. The fundus camera is provided with an observation optical system having an objective lens and a photographing element for photographing a fundus illuminated with illumination light, a monitor on which an image of the photographed fundus is displayed, a fixation-target presenting optical system for presenting a fixation target via the objective lens, a fixation-target moving unit by which a position to present the fixation target is shifted to a desired position, a first display-control unit by which the position of the fixation target is superposed on the fundus image to be displayed on the monitor, and a second display-control unit by which a guide target for moving the fixation target is displayed in a predetermined position on the monitor.

14 Claims, 5 Drawing Sheets

FUNDUS CAMERA

BACKGROUND OF THE INVENTION

1. Field of the Invention

The present invention relates to a fundus camera for photographing a fundus of an eye to be examined.

2. Description of Related Art

Fundus cameras for photographing a periphery of a fundus are known constructed such that an internal fixation target (fixation light) may be moved to guide a line of sight of an examinee. For moving a fixation target, several methods have been suggested, for example, a method by which a point light source as a fixation target is moved with a lever and the like, and a method by which one of a plurality of point light sources provided in predetermined positions is selectively lit. For recognizing a travel position of the fixation target, a method has been suggested by which an image of the fixation target is optically synthesized and displayed together with an image of the fundus on a monitor for observation.

According to the method by which the point light source is moved with the lever and the like, the position of the fixation target maybe recognized through observation on the monitor. However, if a periphery of the fundus is divided every 60° degrees into six sections for photographing to obtain six images, for instance, it is difficult to place the fixation target in each position intended for photographing. On the other hand, according to the method by which one of the plurality of point light sources is selectively lit, the fixation target may be placed in the position intended for photographing provided that coordinates of lighting positions are predetermined. This method, however, ensures only a low degree of freedom for photographing outside the predetermined positions.

SUMMARY OF THE INVENTION

The present invention has been made in view of the above circumstances and has an object to overcome the above problems and to provide a fundus camera capable of moving a fixation target surely and precisely to a position intended for photographing with an adequate degree of freedom for moving the fixation target.

To achieve the objects and in accordance with the purpose of the present invention, as embodied and broadly described herein, a fundus camera for photographing a fundus of an eye to be examined is provided with: an observation optical system; a monitor; a fixation-target presenting optical system; a fixation-target moving unit; a first display-control unit; and a second display-control unit. The observation optical system has an objective lens and a photographing element for photographing the fundus of the eye to be examined via the objective lens while illuminating the fundus with illumination light for observation. An image of the photographed fundus is displayed on the monitor. In the fixation-target presenting optical system, a fixation target is presented via the objective lens to be visually identified by the eye. The fixation-target moving unit shifts a position to present the fixation target to a desired position. The position of the fixation target to be shifted is superposed on the fundus image to be displayed on the monitor by the first display-control unit. A guide target for moving the fixation target is displayed in a predetermined position on the monitor by the second display-control unit.

In another aspect of the invention, the fundus camera is provided with: an observation optical system; a monitor (a display); a fixation-target presenting optical system; a fixation-target moving unit; a first display-control unit; a second display-control unit; and a specifying unit. The observation optical system has an objective lens and a photographing element for photographing the fundus of the eye to be examined via the objective lens while illuminating the fundus with illumination light for observation. An image of the photographed fundus is displayed on the monitor. In the fixation-target presenting optical system, a fixation target is presented via the objective lens to be visually identified by the eye. The fixation-target moving unit shifts a position to present the fixation target to an intended position. The position of the fixation target to be shifted is superposed on the fundus image to be displayed on the monitor by the first display-control unit. The second display unit has a program by which at least one of plural patterns of guide targets for moving the fixation target is displayed in a predetermined position on the monitor. The specifying unit specifies at least one of the plural patterns of the guide targets.

Additional objects and advantages of the invention are set forth in the following description, are obvious from the description, or may be learned by practicing the invention. The objects and advantages of the invention may be realized and attained by means of instrumentalities and combinations particularly pointed out in the claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
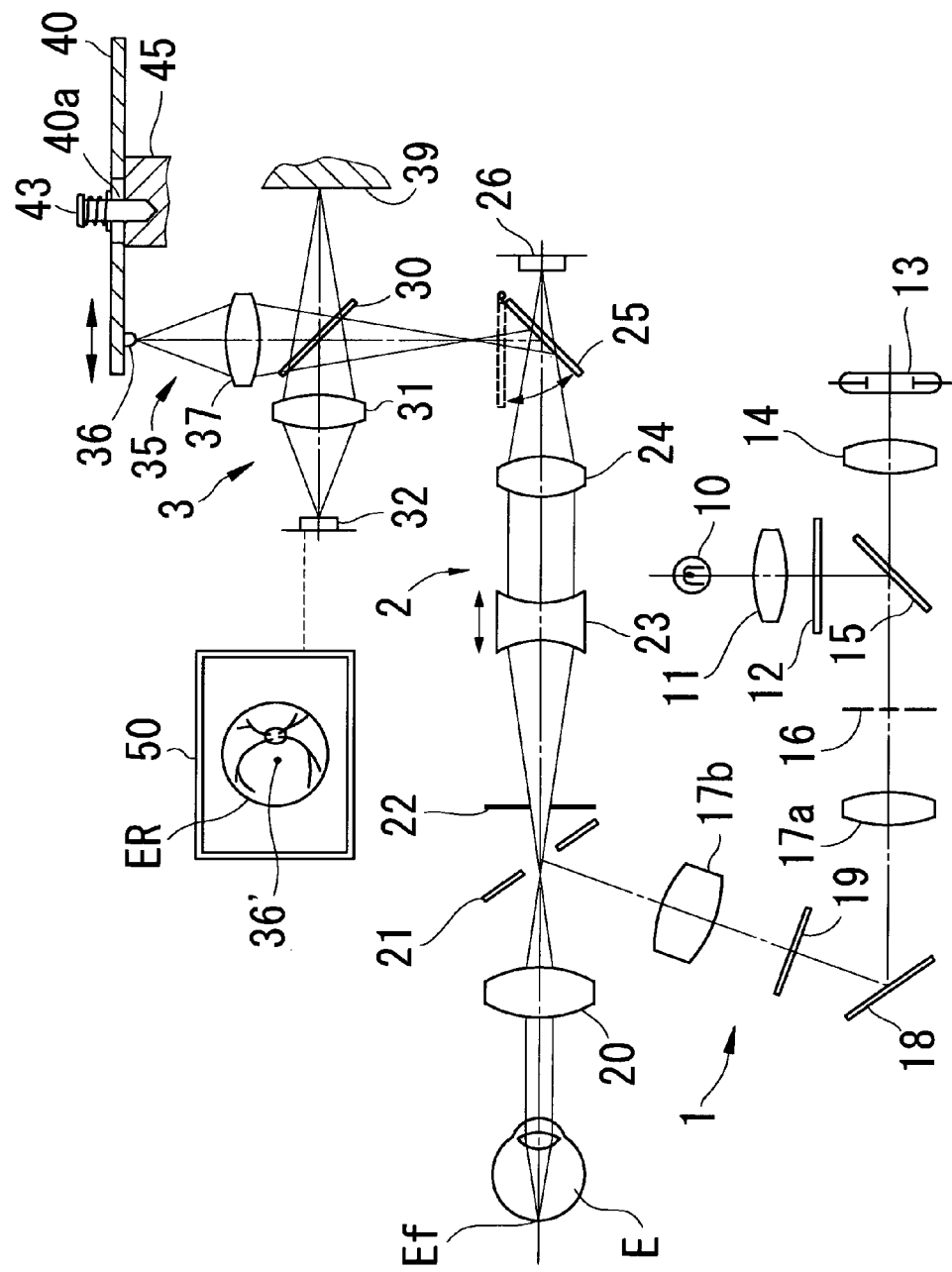
FIG. 1 is a view showing a schematic configuration of an optical system in a fundus camera as one preferred embodiment according to the present invention.

A detailed description of preferred embodiments of a fundus camera consistent with the present invention will now be given referring to the accompanying drawings. FIG. 1 is a view showing a schematic configuration of an optical system in a fundus camera of a non-midriasis type as a first preferred embodiment. The optical system is provided with an illumination optical system 1, a photographing optical system 2, an observation optical system 3 and a fixation-target presenting optical system 35.

<Illumination Optical System>

Illumination light emitted from a halogen lamp 10 being a light source for observation passes through a condenser lens 11 to be converted into infrared illumination light by an infrared filter 12 having a wavelength-selecting property of transmitting infrared light. Thereafter, the light is reflected by a half mirror 15 and illuminates a ring slit 16 having a ring-shaped aperture. Alternatively, instead of the halogen lamp 10, it may be possible to use such an infrared light source as an infrared LED, which would eliminate the need for the filter 12. Besides, instead of the half mirror 15, it may also be possible to use a dichroic mirror having a wavelength-selecting property of reflecting infrared light and transmitting visible light.

Visible illumination light emitted from a flash lamp 13 being a light source for photographing passes through a condenser lens 14, and is transmitted by the half mirror 15 to be made coaxial with the infrared illumination light, so that the visible illumination light illuminates the ring slit 16.

The illumination light having passed through the slit 16 (ring-slit light) forms an intermediate image in the vicinity of an aperture of an apertured mirror 21 via a relay lens 17a, a mirror 18, a black-dot plate 19 with a small black dot on its center, and a relay lens 17b. The light is then reflected to be coaxial with an optical axis of the photographing optical system 2. Once the illumination light (the ring-slit light) reflected by the mirror 21 forms an image via an objective lens 20 in the vicinity of the pupil of an eye E to be examined, the light is diffused to illuminate a fundus Ef of the eye E uniformly. When entering the lens 20, the illumination light (the ring-slit light) may generate some amount of reflected light which would be detrimental at the time of observing and photographing an image of the fundus Ef. Therefore, it is arranged that the detrimental light should be absorbed by a small black dot provided in the center of the black-dot plate 19.

<Photographing Optical System>

Once the light reflected from the fundus Ef forms an intermediate image of the fundus Ef via the lens 20, the reflected light enters a return mirror 25 through the aperture of the mirror 21, a photographic diaphragm 22, a focusing lens 23 movable in the direction of the optical axis, and an image forming lens 24. The return mirror 25 is placed in a position indicated by solid lines at the time of observation while it is placed in a position indicated by broken lines at the time of photographing. The visible light reflected from the fundus Ef, which is not reflected by the return mirror 25 if the mirror 25 is placed in the position of the broken lines, enters a color CCD camera 26 having a sensitivity to the visible region, and then forms an image of the fundus Ef on a photographing surface of the camera 26.

<Observation Optical System>

The return mirror 25 is placed in the position of the solid lines except when photographing is performed.) A half mirror 30 has a reflectance larger than its transmittance. On an optical path in the direction of reflection from the half mirror 30 are disposed a relay lens 31 and a CCD camera 32 for observation having a sensitivity to the visible region through the infrared region. The infrared light reflected from the fundus Ef, which is reflected by the return mirror 25 if the mirror 25 is placed in the position of the solid lines, is further reflected by the half mirror 30, and then enters the camera 32 through the lens 31 to form an image of the fundus Ef on a photographing surface of the camera 23. Output from the camera 32 is inputted to a color monitor 50 which doubles as a monochrome monitor, so that an image ER of the fundus Ef is displayed on the monitor 50.

<Fixation-target Presenting Optical System>

A fixation-target presenting optical system 35 comprises a point light source 36 as a fixation target and a relay lens 37, and shares the optical path from the return mirror 25 to the lens 20 with the observation optical system 3 via the half mirror 30. It is arranged that the point light source 36 should be moved within a plane approximately conjugate with the fundus Ef and the photographing surface of the camera 32 by operating a lever 40. The point light source 36 is mounted on the lever 40. The lever 40, in which an oblong hole 40a is formed, is retained on an enclosure part 45 of the fundus camera by a screw 43 and the like so as to slide smoothly. Part of the lever 40 extends off the enclosure 45, enabling an examiner to operate the lever 40 to move the point light source 36, so that the fundus Ef (a line of sight) may be guided to a desired part for photographing.

A reflecting mirror 39 is provided in the opposite side of the lens 31 beyond the half mirror 30. The mirror 39 is disposed at a position approximately conjugate with the photographing surface of the camera 32 via the lens 31 and also approximately conjugate with the point light source 36 via the lens 37. When the point light source 36 is lit, part of its light is reflected by the half mirror 30 to head for the mirror 39, by which the light is reflected again to return to the mirror 30. Part of the light transmitted by the half mirror 30 forms an image on the photographing surface of the camera 32 via the lens 31. Thus, an image 36' of the fixation target is superposed on the fundus image ER to be displayed on the monitor 50. (The position of the fixation target on the fundus image ER is indicated.)

Figure 2:
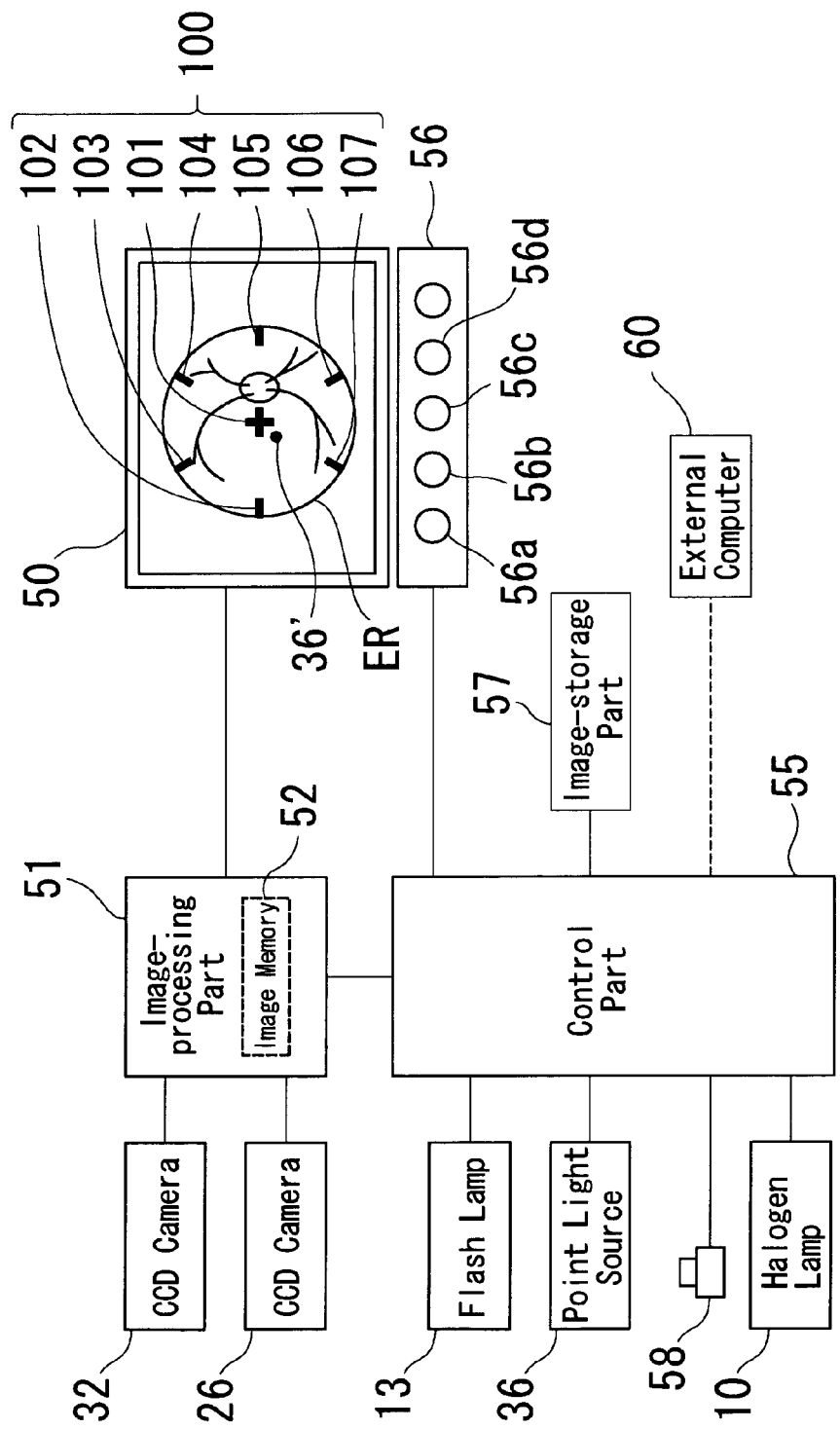
FIG. 2 is a block diagram illustrating a primary part of a control system in the fundus camera as the preferred embodiment shown in FIG. 1.

FIG. 2 is a block diagram illustrating a primary part of a control system in the fundus camera consistent with the present invention. Outputs from the cameras 32 and 26 are inputted to an image-processing part 51, which receives control signals from a control part 55 so as to graphically generate guide targets 100 for guiding the travel position of the fixation target. The image-processing part 51 then superposes the guide targets 100 on the fundus image (an image observed) through the camera 32 and displays the resultant on the monitor 50. The fundus image (an image photographed) with the camera 26 is stored in an image memory 52 contained in the image-processing part 51. Thereafter, outputs from the image-processing part 51 are switched in response to control signals from the control part 55, so that the fundus image ER from the camera 26 is displayed in color on the monitor 50.

Connected to the control part 55 are a switch part 56 including a photographing-mode selection switch 56a, an image-storage part 57, a photographing switch 58, and the like. Also, connected to the control part 55 may be an external computer 60. Image data stored in the image-storage part 57 may be transferred to and outputted on the computer 60.

A description will now be given to operations performed in the above-described configuration. First, how to move the fixation target to a desired position will be explained.

An image of an eye E illuminated with infrared light from the lamp 10 and through the filter 12 is formed on the photographing surface of the camera 32, and the formed image is displayed on the monitor 50. An examiner performs alignment (position adjustments) of a main body of the fundus camera with respect to the eye E. Also, he moves the lens 23 to achieve proper focus. When he lights the point light source 36, the light is collected into the fundus Ef through the lens 37, the half mirror 30, the return mirror 25, the lens 24, the lens 23, the diaphragm 22, the aperture of the mirror 21, and the lens 20. Thus, an examinee (the eye E) visually identifies the point light source 36 as a fixation target, and a line of sight of the examinee (the eye E) is guided accordingly.

Part of the light emitted from the point light source 36, which has been reflected by the mirror 30, is further reflected by the mirror 39, and the reflected light forms an image on the photographing surface of the camera 32 via the half mirror 30 and the lens 31. As a result, the fixation-target image 36' is displayed on the monitor 50 as well as the fundus image ER.

While observing the fundus image ER and the fixation-target image 36' on the monitor 50, the examiner operates the lever 40 to move the point light source 36 to a desired position so that he may observe a desired part of the fundus Ef. When he determines a position to be photographed, he depresses the switch 58 to perform photographing.

Figure 3:
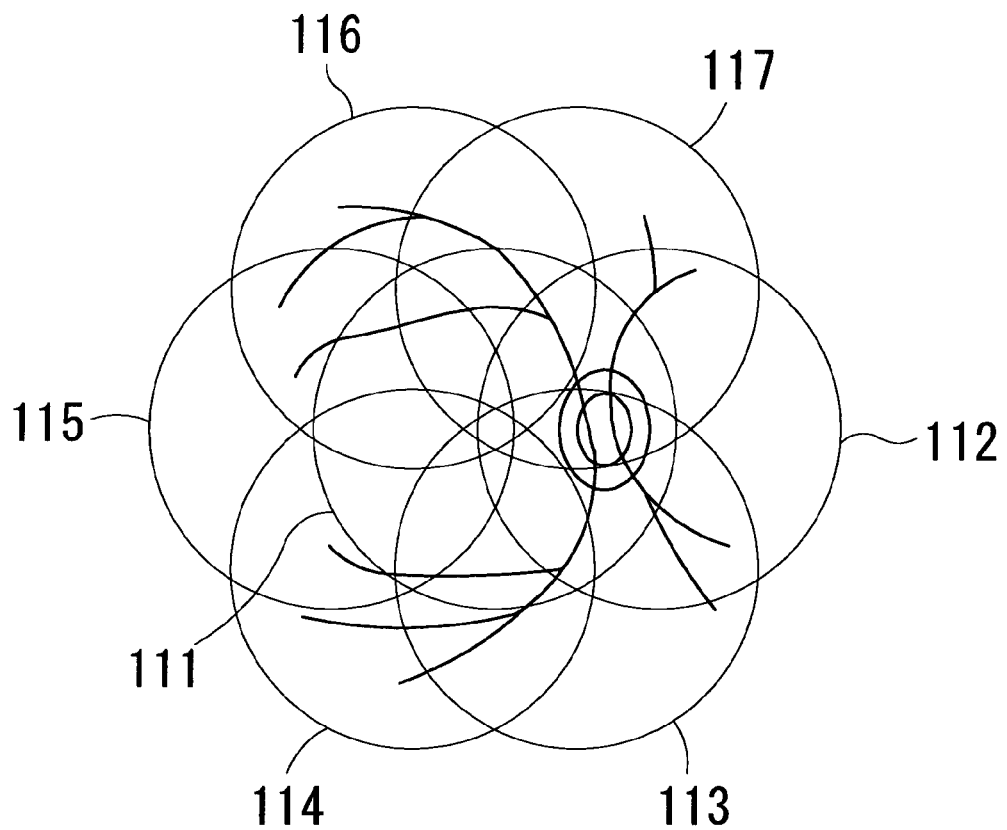
FIG. 3 is a view illustrating a case of obtaining an image of a fundus photographed with its posterior pole appearing in the center and six images of a periphery of the fundus photographed with its circumference divided every 60° degrees.
Figure 4:
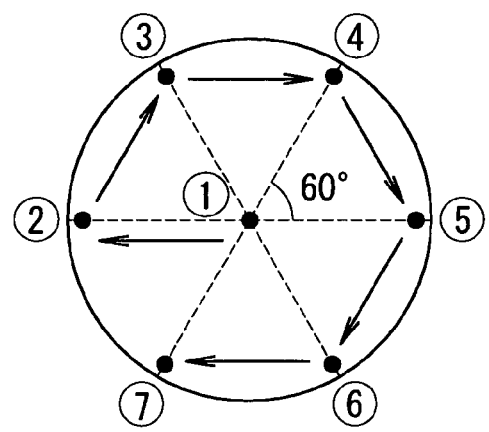
FIG. 4 is a view showing a sequence of moving an image of a fixation target on a monitor and photographing through the use of the fundus camera to obtain each image shown in FIG. 3.

Next, an explanation will now be given to a fundus image 111 obtained by photographing a posterior pole of the fundus Ef such that it appears in the center and six fundus images 112–117 obtained by splitting a periphery of the posterior pole every 60° degrees and by photographing each section as shown in FIG. 3. These kinds of fundus images are needed for examining such a disease as diabetic retinopathy. FIG. 4 shows a sequence of photographing while moving the fixation-target image 36' to seven spots in total from the center to the periphery (of which circumference is split every 60° degrees) on the monitor 50 in order to obtain the images shown in FIG. 3.

Prior to photographing, a guide-target displaying mode is selected with the switch 56a. When this mode is selected, a cross mark 101 indicating the center and six peripheral line marks 102–107 splitting the circumference every 60° degrees are graphically synthesized to be displayed as the guide targets 100 on the monitor 50 where the fundus image ER and the fixation-target image 36' are displayed (see FIG. 2.)

The examiner moves the point light source 36 according to the guide targets 100 displayed on the monitor 50. First, in order to photograph a first image, namely, the fundus image 111 in which the posterior pole appears in the center, he moves the point light source 36 by operating the lever 40 so as to place the fixation-target image 36' in the center of the position where the cross mark 101 is displayed. After having guided the line of sight of the examinee (the eye E) successfully by moving the point light source 36, he depresses the switch 58 to obtain a fundus image. When trigger signals from the switch 58 are consequently inputted to the control part 55, the control part 55 lays the return mirror 25 in the position of the broken lines and lights the lamp 13 to illuminate the fundus Ef with visible light. The light reflected from the fundus Ef travels along the optical path of the photographing optical system 2 to enter the photographing surface of the camera 26, so that the fundus image is obtained.

When the image photographed with the camera 26 is stored in the image memory 52, the image thus stored is displayed as a still-frame image on the monitor 50 by the image-processing part 51. The examiner checks the image, and if it is sharp enough, he depresses an image-storage switch 56b and proceeds to photograph the next part. When the switch 56b is depressed, the image stored in the image memory 52 is transferred to and stored in the image-storage part 57. If the photographed image is not sharp enough, the examiner depresses a cancellation switch 56c to redo the photographing.

The depression of the switch 56b or 56c changes the display on the monitor 50 to the image observed from the camera 32, and the guide targets 100 are then displayed, superposed on the fundus image ER (the observed image.)

In order to photograph a second image, namely, the image 112 of the periphery of the fundus Ef, the examiner moves the point light source 36 by operating the lever 40 so as to place the fixation-target image 36' in a position where the line mark 102 is displayed, and then performs photographing. Subsequently, in a like manner, the fundus images 113, 114, 115, 116 and 117 may be obtained by photographing while moving the point light source 36 so as to place the fixation-target image 36' sequentially in the positions where the line marks 103, 104, 105, 106 and 107 are each displayed. Thus, the present preferred embodiment adopts a method by which the fixation target may be moved arbitrarily while it is presented. The method therefore enables the line of sight of the examinee to follow a movement of the fixation target more easily than a method by which a position for the fixation target to be displayed is changed over selectively.

It should be noted that, in photographing with reference to the above-mentioned guide targets 100, the examiner may distinguish easily which part is to be photographed if a display form of the respective marks of the guide targets 100 varies according to the sequence of photographing. In photographing with the fixation-target image 36' moved in the above-described sequence, for example, the image-processing part 51 blinks the cross mark 101 first. Upon input of photographing-completion signals with a depression of the switch 56b, the image-processing part 51 blinks the line mark 102 for the next part to be photographed. Subsequently, upon every input of the photographing-completion signals, the image-processing part 51 blinks the line marks 103–107 in sequence so as to notify the examiner about the shift in the travel position of the fixation target. This process may prevent the examiner from skipping any intended part to be photographed. The respective marks of the guide targets 100 may be designed not to blink but to change their color instead, or it may be possible to display only one mark in the position to which the fixation target should be moved. In those cases, the sequence of photographing is preprogrammed and stored in a memory in the control part 55, which instructs the image-processing part 51 to change the display form of the guide targets 100.

Otherwise, the respective marks of the guide targets 100 may also be designed such that one of the marks disappears or changes its color when the fixation target is positioned at that particular mark or when the fixation target is positioned at the particular mark and the photographing is then completed (i.e. the trigger signals for photographing are inputted, or the photographing-completion signals are inputted, or the like.) That allows the examiner to be notified about the completion of the photographing, dispensing with any preprogrammed sequence of photographing. In this case, the control part 55 detects the travel position of the fixation target by detecting via the image-processing part 51 the position of the fixation-target image 36' which has entered the camera 32. The position of the fixation-target image 36' is detected based on its size and quantity of light. (Since the quantity of light from the point light source 36 is larger than the fundus-reflected light which is rather feeble, a threshold level of the light quantity may be a basis of the detection.) Alternatively, the detection of the travel position of the point light source 36 may also be made possible by providing a light-beam separation mirror between the half mirror 30 and the reflecting mirror 39 and by disposing a two-dimensional position-detecting sensor such as PSD in the direction of light-beam separation. In addition, another alternative is to provide the vicinity of the point light source 36 with a sensor detecting the travel position of the point light source 36 so that the travel position of the fixation target is detected directly.

Figure 5:
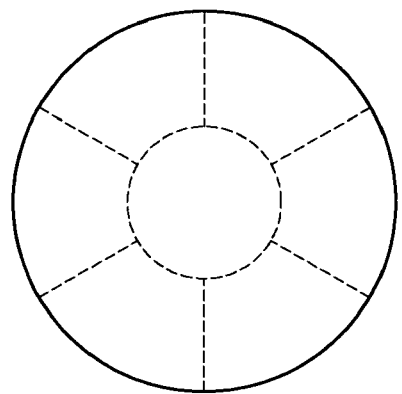
FIG. 5 is a view showing an example of detecting a travel position of the fixation target in an area divided into seven sections.

The travel position of the fixation target does not necessarily have to be detected precisely; it is sufficient to find a positional relationship of the fixation target with respect to the part to be photographed. Accordingly, the travel position of the fixation target is detected in each section of a seven-divided area as indicated by dotted lines in FIG. 5.

As described above, moving the point light source 36 according to the guide targets 100 may facilitate and ensure proper photographing of the periphery of a fundus in intended positions or at predetermined angles.

In addition, the images thus obtained mean that the line of sight has been guided based on proper positional relationships. A panoramic image of good quality may therefore be created when the images stored in the image-storage part 57 are transmitted to, and are linked together by the external computer 60.

It should be noted that the guide targets are not limited to the above patterns; an optimum pattern of the guide targets may be selected from a plurality of patterns corresponding with various types of photographing. The plurality of patterns are preprogrammed and stored in the memory in the control part 55, and the selected pattern is displayed by the image-processing part 51 under instructions from the control part 55 in correspondence with a selection made with a guide-target selection switch 56d.

Figure 7:
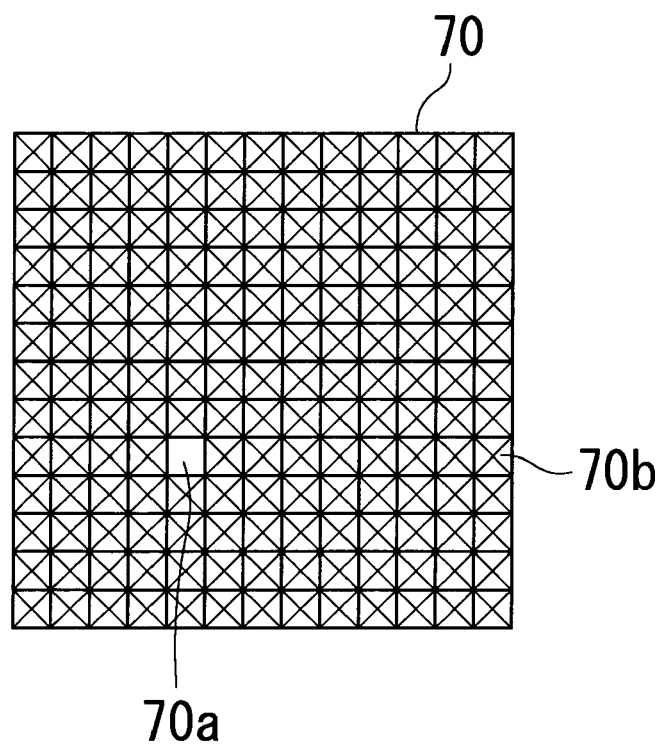
FIG. 7 is a view illustrating a method of forming the fixation target with a liquid crystal display in the second embodiment shown in FIG. 6.
Figure 6:
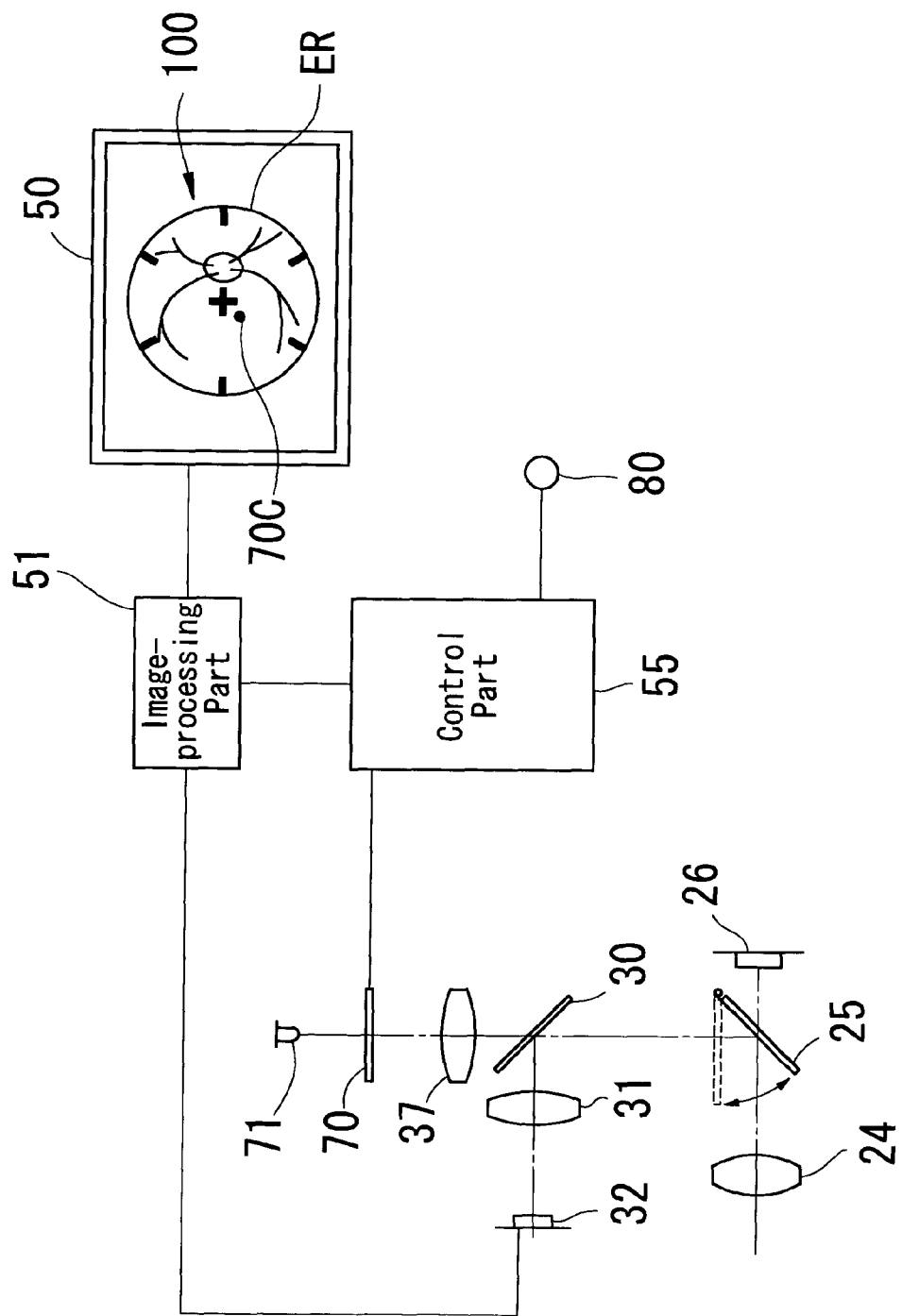
FIG. 6 is a view showing a partial schematic configuration of the optical system and the control system exemplifying a modification of fixation-target presentation as a second embodiment according to the present invention.

FIG. 6 is a partial schematic view showing a second preferred embodiment, namely, a modification of the fixation-target presentation; an example in which, in contrast to the first preferred embodiment, a liquid crystal display (LCD) 70 is employed as a point light source for the fixation target to be moved to a desired position. The LCD 70 is disposed at a position approximately conjugate with the fundus Ef and the photographing surface of the camera 32, and a light source 71 is disposed behind the LCD 70. As shown in FIG. 7, the control part 55 controls placement of a light-transmitting portion (aperture) 70a and a light-shielding portion 70b both included in the LCD 70. The transmitting portion 70a is illuminated by the light source 71 so as to function as a point light source. The lighting position (the position of the transmitting portion 70a) may be shifted to a desired position by an examiner operating a fixation-target shift switch 80 such as a cross key.

According to the second preferred embodiment, the fixation target (the fixation-target image 36') to be displayed on the monitor 50 is electrically synthesized, while it is optically synthesized according to the first preferred embodiment. To be more specific, operating the switch 80 connected to the control part 55 shifts the position of the transmitting portion 70a and its positional information is converted into electronic signals to be captured by the control part 55. With reference to the positional information, a character 70C, which has been generated by the image-processing part 51, is superimposed on a fundus image ER to be displayed on the monitor 50. (The position of the fixation target on the fundus image ER is indicated.) Since the guide targets 100 are also displayed on the monitor 50 in the second preferred embodiment, the fixation target is moved with the switch 80 such that the character 70C is placed at one of the marks of the guide targets 100 as appropriate for photographing. As a matter of course, the display form of the guide targets 100 may be varied.

As described up to this point, according to the present invention, a fixation target may be moved surely and precisely to a position intended for photographing while an adequate degree of freedom is secured for moving the fixation target.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A fundus camera comprising:

an observation optical system having an objective lens and a first camera, for obtaining an observation image of a fundus of an eye to be examined via the objective lens, the fundus being illuminated with illumination light for observation;

a photographing optical system having a second camera, for obtaining a photographed image of the fundus via the objective lens, the fundus being illuminated with illumination light for photographing, wherein an optical axis of the photographing optical system has a predetermined positional relationship with an optical axis of the observation optical system;

a monitor which displays the obtained fundus observation image;

a fixation-target presenting optical system for presenting a fixation target to the fundus via the objective lens so that the presented fixation target guides a line of vision of the eye, wherein an optical axis of the fixation-target presenting optical system has a predetermined positional relationship with the optical axis of the photographing optical system;

a fixation-target moving unit having operation means, that freely moves the fixation target in a region of a two-dimensional plane orthogonal to the optical axis of the fixation-target presenting optical system;

a first display-control unit which having control to optically or electrically display on the displayed fundus observation image an indicator to indicate a presented position of the fixation target on the fundus; and a second display-control unit which having control to graphically display on the displayed fundus observation image a guide target for guiding movement of the fixation target;

wherein moving the fixation target so that the displayed indicator is positioned at the displayed guide target the moved fixation target guides the line of vision to a predetermined direction.

2. The fundus camera according to claim 1, wherein the second display-control unit has control to graphically display the guide target in a plurality of predetermined positions on the displayed fundus observation image.

3. The fundus camera according to claim 2, wherein the second display-control unit has control to vary a display form of the guide target in accordance with a predetermined sequence.

4. The fundus camera according to claim 2, further comprising a sensor which detects that the indicator has been moved to each predetermined position, wherein the second display-control unit has control to vary a display form of the guide target based on a result detected by the sensor.

5. The fundus camera according to claim 2, wherein the second display-control unit has control to vary a display form of the guide target in response to input of a trigger signal for photographing or a photographing-completion signal.

6. The fundus camera according to claim 1, wherein
the fixation-target presenting optical system has a point light source, and
the fixation-target moving unit includes a light-source moving unit which moves the point light source.

7. The fundus camera according to claim 1, wherein
the fixation-target presenting optical system comprises a liquid crystal display with a light source behind, and
the fixation-target moving unit includes a screen-control unit which moves a position of a light-transmitting portion on the liquid crystal display.

8. The fundus camera according to claim 1, further comprising a mode-selecting unit which determines whether the guide target should be displayed on the monitor or not.

9. The fundus camera according to claim 1,
wherein the second display-control unit has a memory in which plural guide targets of different patterns are stored and has control to display a selected guide target.

10. A fundus camera comprising:
an observation optical system having an objective lens and a first camera, that obtains an observation image of a fundus of an eye to be examined via the objective lens, the fundus being illuminated with illumination light for observation;
a photographing optical system having a second camera, that obtains a photographed image of the fundus via the objective lens, the fundus being illuminated with illumination light for photographing, wherein an optical axis of the photographing optical system has a predetermined positional relationship with an optical axis of the observation optical system;
a monitor which displays the obtained fundus observation image;
a fixation-target presenting optical system for presenting a fixation target to the fundus via the objective lens so that the presented fixation target guides a line of vision of the eye, wherein an optical axis of the fixation-target presenting optical system has a predetermined positional relationship with the optical axis of the photographing optical system;
a fixation-target moving unit having operation means, that freely moves the fixation target in a region of a two-dimensional plane orthogonal to the optical axis of the fixation-target presenting optical system;
a first display-control unit which has control to optically or electrically display on the displayed fundus observation image an indicator to indicate a presented position of the fixation target on the fundus; and
a second display-control unit having a program by which a guide target for guiding movement of the fixation target is displayed graphically in a plurality of predetermined positions on the displayed fundus observation image and a display form of the guide target is varied based on a sequence of photographing of plural parts of the fundus,
wherein by moving the fixation target so that the displayed indicator is positioned at the display guide target, wherein the moved fixation target guides the line of vision to a predetermined direction.

11. The fundus camera according to claim 10,
wherein the program varies the display form of the guide target in accordance with a predetermined sequence of photographing of the plural parts.

12. The fundus camera according to claim 10, further comprising a sensor which detects that the indicator has been moved to each predetermined position, and
wherein the program varies the display form of the guide target based on a result detected by the sensor.

13. The fundus camera according to claim 10,
wherein the program varies the display form of the guide target in response to input of a trigger signal for photographing or a photographing-completion signal of each of the plural parts.

14. The fundus camera according to claim 10,
wherein the second display-control unit has a memory in which plural guide targets of different patterns are stored and has control to display a selected guide target in the predetermined positions.

* * * * *